(12) United States Patent
Asada et al.

(10) Patent No.: US 8,329,649 B2
(45) Date of Patent: Dec. 11, 2012

(54) AQUEOUS COMPOSITION CONTAINING FOLLICLE-STIMULATING HORMONE AND HISTIDINE

(75) Inventors: Hajime Asada, Tokyo (JP); Hiroshige Kataoka, Kanagawa (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/127,108

(22) PCT Filed: Nov. 2, 2009

(86) PCT No.: PCT/JP2009/005809
§ 371 (c)(1),
(2), (4) Date: Jul. 20, 2011

(87) PCT Pub. No.: WO2010/052879
PCT Pub. Date: May 14, 2010

(65) Prior Publication Data
US 2011/0275567 A1    Nov. 10, 2011

(30) Foreign Application Priority Data

Nov. 4, 2008  (JP) ................................ 2008-283079
Sep. 18, 2009 (JP) ................................ 2009-216563

(51) Int. Cl.
*A61K 38/24* (2006.01)
*C07K 14/59* (2006.01)

(52) U.S. Cl. ........................................ 514/9.9; 530/399

(58) Field of Classification Search ................... None
See application file for complete search history.

(56) References Cited

U.S. PATENT DOCUMENTS

| 4,297,344 | A | 10/1981 | Schwinn et al. |
| 4,440,679 | A | 4/1984 | Fernandes et al. |
| 5,140,010 | A | 8/1992 | Goldstein et al. |
| 5,929,028 | A | 7/1999 | Skrabanja et al. |
| 2002/0172933 | A1 | 11/2002 | Romisch et al. |
| 2004/0038878 | A1 | 2/2004 | Tanikawa et al. |
| 2006/0147480 | A1* | 7/2006 | Samaritani et al. ........... 424/400 |
| 2007/0122402 | A1 | 5/2007 | Bolli et al. |
| 2011/0275567 | A1* | 11/2011 | Asada et al. ................... 514/9.9 |

FOREIGN PATENT DOCUMENTS

| DE | 19856443 | 1/1968 |
| DE | 2916711 | 4/1979 |
| JP | 4-502017 | 4/1992 |
| JP | 8-333277 | 12/1996 |
| JP | 10-203997 | 8/1998 |
| JP | 2002-275090 | 9/2002 |
| JP | 2007-511566 | 5/2007 |
| JP | 2009-509953 | 3/2009 |
| WO | 02/11753 | 2/2002 |
| WO | 2004/087213 | 10/2004 |
| WO | 2007/037607 | 4/2007 |
| WO | 2008/084237 | 7/2008 |

OTHER PUBLICATIONS

Uedaira et al., "The Effect of Sugars on the Thermal Denaturation of Lysozyme", Bull. Chem. Soc. Jpn., 1980, pp. 2451-2455.
Lee et al., "The Stabilization of Proteins by Sucrose", J. Biol. Chem., 1981, pp. 7193-7201.
Charman et al., "Techniques for Assessing the Effects of Pharmeceutical Excipients on the Aggregation of Porcine Growth Hormone", Pharm. Res, 1993, pp. 954-962.
Wang et al., "Thermal-induced Denaturation of Two Model Proteins: effect of poloxamer 407 on solution stability", Int. J. Pharm., 1993, pp. 41-49.
Powell et al., "Parenteral Peptide Formulations: Chemical and Physical Properties of Native Luteinizing Hormone-Releasing Hormone (LHRH) and Hydrophobic Analogues in Aqueous Solution", Pharm. Res., 1991, pp. 1258-1263.
Tsai et al., "Formulation Design of Acidic Fibroblast Growth Factor", Pharm. Res., 1993, pp. 649-659.
International Preliminary Report on Patentability issued with respect to International Application No. PCT/JP2009/005809 filed Nov. 2, 2009, mailed May 19, 2011.
European Search Report issued with respect to counterpart European Application No. 09824580.6, dated Jul. 10, 2012.

* cited by examiner

*Primary Examiner* — Zachary Howard
(74) *Attorney, Agent, or Firm* — Greenblum & Bernstein, P.L.C.

(57) ABSTRACT

A stable aqueous composition containing follicle-stimulating hormone, which comprises follicle-stimulating hormone and histidine as a stabilizing agent.

13 Claims, 3 Drawing Sheets

AQUEOUS COMPOSITION CONTAINING FOLLICLE-STIMULATING HORMONE AND HISTIDINE

TECHNICAL FIELD

The present invention relates to a stable aqueous composition containing follicle-stimulating hormone.

BACKGROUND ART

Follicle-stimulating hormone (henceforth also abbreviated as "FSH") is a hormone synthesized and secreted by gonadotrophic hormone-producing cells of the anterior pituitary. FSH has an action of stimulating growth of immature ovarian follicles and ripening the cells in the ovary. As a medicament, FSH has been used as an ovulation-inducing agent in the assisted reproductive technology (ART).

Preparations of human menopausal gonadotropin (hMG) extracted from postmenopausal women's urine have been conventionally used as FSH-containing compositions. The hMG preparations contain FSH and lutenizing hormone (LH) in which the activity ratio of FSH and LH is about 1:1. In foreign countries, "recombinant FSH preparations" produced by gene recombination without using human urine as a raw material have recently been mainly used, and also in Japan, Follistim (registered trademark) was approved in 2005. Since these recombinant preparations do not use urine as a raw material, they are featured not to contain impurities and have consistent quality.

Bio-active proteins are generally unstable in a state of an aqueous solution, and this tendency is enhanced when purity of a protein becomes higher. In aqueous solutions, proteins are hydrolyzed in the same manner as low molecular weight compounds, as well as cause chemical changes such as racemization, and further cause changes of higher-order structures (physical changes) since they are polymer compounds. Examples of such physical changes include denaturation, aggregation, adsorption, precipitation, and the like. In the process of the physical change, it is considered that denaturation occurs as a trigger, and such phenomena as aggregation, adsorption and precipitation are subsequently caused. The denaturation means changes of the three-dimensional structures (tertiary and quaternary structures) such as unfolding of folded chains, and since the denaturation leads loss of physiological activity in most cases, it is important to prevent denaturation for enhanced stability of protein or peptide preparations.

In order to suppress chemical and physical changes in protein preparations, contaminant proteins such as human serum albumin have been generally added as a stabilizing agent. However, to avoid the risk of contamination of viruses and the like, use of recombinant preparations has recently become the mainstream. For the recombinant preparations, various stabilization methods have been examined as substitutes for the addition of contaminant proteins.

For example, it has been investigated to increase stability of protein preparations by adding a compound having an action of forming a hydrogen bond with a protein molecule or enhancing hydration of a protein molecule, such as saccharides, surfactants, and amino acids (see, for example, Bull. Chem. Soc. Jpn., 53, pp. 2451-2455, 1980; J. Biol. Chem., 256, pp. 7193-7201, 1981; Pharm. Res., 10, pp. 954-962, 1993; Int. J. Pharm., 96, pp. 41-49, 1993; Pharm. Res., 8, pp. 1258-1263, 1991; Pharm. Res., 10, pp. 649-659, 1993, and the like). As for amino acids among such compounds, DE-A-2916711, for example, discloses that glycine, α- or β-alanine, proline, glutamine, and the like have a stabilization effect for the blood coagulation factors, and U.S. Pat. No. 4,440,679 describes that arginine, lysine, and/or glycine has a stabilization effect for the VIII factor, fibronectin, and the like. DE-A-1985644 also discloses that arginine, lysine, histidine, phenylalanine, tryptophan, tyrosine, aspartic acid, and/or glutamic acid has a stabilization effect for antithrombin III. However, the stabilization effects of these amino acids are specific to the target proteins or peptides, and therefore, amino acids or combinations of two or more kinds of amino acids having the most effective stabilization effect for arbitrary proteins or peptides cannot be predicted from these findings.

As for FSH, for example, it is described in Patent document 1 that methionine stabilizes gonadotropin in an aqueous composition. Further, as for the stabilization effect of histidine for proteins, it is known that, for example, histidine has a stabilization effect in liquid preparations of blood coagulation factor-related protein (Patent document 2), immunoglobulin (Patent document 3), erythropoietin (Patent document 4), and the like. Furthermore, Patent document 5 discloses a FSH preparation containing glycine, methionine, a nonionic surfactant, and a phosphate buffering agent as stabilizing agents. However, it is not known so far whether histidine has a stabilization effect for FSH in an aqueous composition. It is also not known whether a combination of histidine and another amino acid has a stabilization effect for FSH in an aqueous composition.

PRIOR ART REFERENCES

Patent Documents

Patent document 1: Japanese Patent Unexamined Publication (KOKAI) No. 10-203997
Patent document 2: Japanese Patent Unexamined Publication (KOKAI) No. 2002-275090
Patent document 3: Japanese Patent Unexamined Publication (KOHYO) No. 2007-511566
Patent document 4: International Patent Publication WO02/011753
Patent document 5: Japanese Patent Unexamined Publication (KOHYO) No. 2009-509953
Patent document 6: DE-A-2916711
Patent document 7: U.S. Pat. No. 4,440,679
Patent document 8: DE-A-19856443

Non-Patent Documents

Non-patent document 1: Bull. Chem. Soc. Jpn., 53, pp. 2451-2455, 1980
Non-patent document 2: J. Biol. Chem., 256, pp. 7193-7201, 1981
Non-patent document 3: Pharm. Res., 10, pp. 954-962, 1993
Non-patent document 4: Int. J. Pharm., 96, pp. 41-49, 1993
Non-patent document 5: Pharm. Res., 8, pp. 1258-1263, 1991
Non-patent document 6: Pharm. Res., 10, pp. 649-659, 1993

SUMMARY OF THE INVENTION

Object to be Achieved by the Invention

An object of the present invention is to provide an aqueous composition containing follicle-stimulating hormone. More specifically, the object of the present invention is to provide a means for stabilizing follicle-stimulating hormone in an aqueous composition using an amino acid.

Means for Achieving the Object

The inventors of the present invention conducted various researches about substances that stabilizing follicle-stimulating hormone in the state of an aqueous solution, and found that histidine had an extremely superior stabilization effect, and achieved further higher stabilization effect when appropriately combined with another amino acid, saccharide, buffer, or the like. The present invention was accomplished on the basis of the aforementioned findings.

The present invention thus provides an aqueous composition comprising follicle-stimulating hormone and histidine as a stabilizing agent.

According to preferred embodiments of the present invention, there are provided the aforementioned aqueous composition, wherein concentration of histidine is 0.05 to 10.0 mg/mL; the aforementioned aqueous composition, wherein concentration of histidine is 0.2 to 5.0 mg/mL; and the aforementioned aqueous composition, wherein concentration of histidine is 0.25 to 2.0 mg/mL. According to a preferred embodiment of the present invention, there is also provided the aforementioned aqueous composition, which further comprises methionine, and according to more preferred embodiments, there are provided the aforementioned aqueous composition, wherein concentration of methionine is 0.05 to 10.0 mg/mL; the aforementioned aqueous composition, wherein concentration of methionine is 0.2 to 5.0 mg/mL; and the aforementioned aqueous composition, wherein concentration of methionine is 0.25 to 2.0 mg/mL. Furthermore, there is also provided the aforementioned aqueous composition, which comprises a genetic recombinant human follicle-stimulating hormone as the follicle-stimulating hormone.

According to preferred embodiments of the present invention, there are provided the aforementioned aqueous composition, which further comprises one or two or more kind of substances selected from the group consisting of a saccharide, propylene glycol and creatinine; and the aforementioned aqueous composition, which further comprises one or two or more kinds of substances selected from the group consisting of xylitol, inositol, propylene glycol, sucrose, calcium gluconate, sodium gluconate, mannitol, macrogol 600 and creatinine.

According to a more preferred embodiment of the present invention, there is provided the aforementioned aqueous composition, which further comprises a surfactant. According to more preferred embodiments of the present invention, there are provided the aforementioned aqueous composition, wherein the surfactant is a surfactant selected from the group consisting of an ionic surfactant, an amphoteric surfactant, and a nonionic surfactant; the aforementioned aqueous composition, wherein the surfactant is a nonionic surfactant; the aforementioned aqueous composition, wherein the surfactant consists of Tween 80 and/or Tween 20; and the aforementioned aqueous composition, wherein the surfactant is Tween 80.

According to another preferred embodiment of the present invention, there is provided the aforementioned aqueous composition, which further comprises a buffering agent. According to more preferred embodiments, there are provided the aforementioned aqueous composition, which comprises a buffering agent selected from the group consisting of a phosphate buffering agent, a citrate buffering agent, an acetate buffering agent, a borate buffering agent, a tartrate buffering agent and a tris buffering agent; the aforementioned aqueous composition, which comprises a phosphate buffering agent or a citrate buffering agent; the aforementioned aqueous composition, which has a pH value of 6.5 to 8.0, preferably 7.0 to 7.8; the aforementioned aqueous composition, which comprises an tonicity agent; the aforementioned aqueous composition, wherein the tonicity agent is sodium chloride; the aforementioned aqueous composition, which further comprises a polycarboxylic acid selected from the group consisting of EDTA, citric acid, phytic acid, malic acid and gluconic acid; the aforementioned aqueous composition, wherein the polycarboxylic acid is EDTA; and the aforementioned aqueous composition, wherein aqueous medium is phosphate buffered saline.

From another aspect of the present invention, there are provided an agent for stabilizing an aqueous solution containing follicle-stimulating hormone as an active ingredient, which comprises histidine; and the above stabilizing agent, which comprises histidine and methionine.

From a still further aspect of the present invention, there are provided a method for stabilizing an aqueous solution containing follicle-stimulating hormone as an active ingredient, which comprises the step of adding histidine and methionine to the aqueous solution; and the aforementioned method, which comprises the step of adding histidine and methionine.

Effect of the Invention

In the aqueous composition of the present invention, follicle-stimulating hormone is stabilized with histidine, and thus chemical and physical changes of the follicle-stimulating hormone are substantially reduced or eliminated. Therefore, the composition is useful as a stable pharmaceutical composition in which reduction of the activity of the hormone is eliminated during storage and distribution.

MODES FOR CARRYING OUT THE INVENTION

Figure 1:
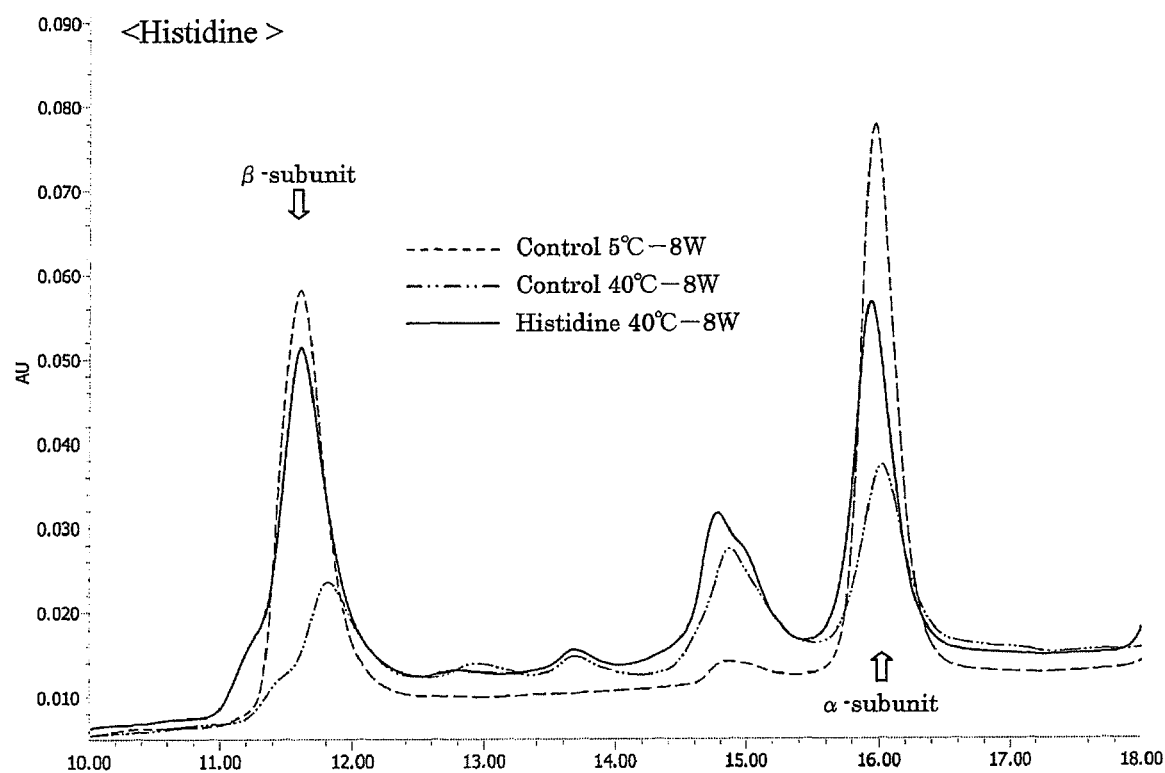
FIG. 1 shows an enlarged view of HPLC charts obtained for follicle-stimulating hormone-containing compositions around the peaks of the α-subunit and β-subunit. The charts were obtained for a composition prepared by adding a genetic recombinant FSH at 150 IU/mL, sucrose at 50 mg/mL and Tween 80 at 0.01% to 10 mM PBS, and further adding histidine to the mixture, after storage thereof at 40° C. for 8 weeks, and a composition prepared by adding a genetic recombinant FSH at 150 IU/mL and Tween 80 at 0.01% to 10 mM PBS, after storage thereof at 5° C. or 40° C. for 8 weeks.

In the present invention, natural follicle-stimulating hormone separated from human urine can also be used. The effect of the present invention is remarkably exhibited where highly purified follicle-stimulating hormone is used. Accordingly, it is preferable to use highly purified follicle-stimulating hormone, preferably highly purified follicle-stimulating hormone substantially consisting of the single substance. According to the present invention, it is preferable to use, from the above point of view, human follicle-stimulating hormone prepared by a genetic recombination technique and substantially free from contaminant proteins as the follicle-stimulating hormone.

A concentration of the follicle-stimulating hormone in the aqueous composition of the present invention is not particularly limited. The concentration is, for example, about 50 to 500 IU/mL, preferably about 100 to 300 IU/mL. The international unit (IU) of follicle-stimulating hormone is described in the document about international standard of FSH by NIBSC (National Institute for Biological Standards and Control, www.nibsc.ac.uk/documents/ifu/98-704.pdf), or the like.

A concentration of histidine in the aqueous composition of the present invention is also not particularly limited. The concentration is, for example, about 0.05 to 10.0 mg/mL, preferably about 0.2 to 5.0 mg/mL, more preferably about 0.25 to 2.0 mg/mL. Although a concentration of methionine in the aqueous composition of the present invention is also not particularly limited, the concentration is, for example, about 0.05 to 10.0 mg/mL, preferably about 0.2 to 5.0 mg/mL, more preferably about 0.25 to 2.0 mg/mL.

The aqueous composition of the present invention may further contain one kind or two or more kinds of substances selected from the group consisting of a saccharide, propylene glycol and creatinine. As the saccharide, monosaccharides, disaccharides, sugar alcohols, aldonic acids and salts thereof, cyclitols, macrogols, and the like can be used. Examples of the monosaccharides include, for example, glucose, mannose, galactose, fructose, xylose, threose, and the like, examples of the disaccharides include, for example, sucrose, maltose, lactose, cellobiose, trehalose, and the like, and examples of the sugar alcohols include, for example, mannitol, xylitol, sorbitol, erythritol, glycerol, and the like. Examples of the aldonic acids or salts thereof include, for example, gluconic acid, galactonic acid, mannonic acid, and the like, and salts thereof, examples of the cyclitols include inositol, and examples of the macrogols include macrogol 200, macrogol 300, macrogol 400, macrogol 600, macrogol 1000, macrogol 1500, macrogol 1540, macrogol 4000, macrogol 6000, macrogol 10000, macrogol 20000, and the like.

The aqueous composition of the present invention can preferably contain one or two or more kinds of substances selected from the group consisting of xylitol, inositol, propylene glycol, sucrose, calcium gluconate, sodium gluconate, mannitol, macrogol 600 and creatinine.

When the aqueous composition of the present invention contains sucrose, mannitol or inositol as the saccharide, the saccharide can be used at a concentration of, for example, about 25 to 125 mg/mL, and can be preferably added at a concentration of about 50 to 100 mg/mL. When xylitol is contained as the saccharide, xylitol can be used at a concentration of, for example, about 1 to 100 mg/mL, and can be preferably added at a concentration of about 5 to 75 mg/mL. When calcium gluconate or sodium gluconate is contained as the saccharide, the gluconate can be used at a concentration of, for example, about 0.2 to 75 mg/mL, and can be preferably added at a concentration of about 1 to 50 mg/mL. When macrogol 600 is contained as the saccharide, the surfactant can be used at a concentration of, for example, about 0.2 to 75 mg/mL, and can be preferably added at a concentration of about 1 to 50 mg/mL. When propylene glycol is contained, the glycol can be used at a concentration of, for example, about 1 to 100 mg/mL, and can be preferably added at a concentration of about 5 to 75 mg/mL. When creatinine is contained, creatinine can be used at a concentration of, for example, about 0.1 to 50 mg/mL, and can be preferably added at a concentration of about 0.5 to 30 mg/mL.

The aqueous composition of the present invention may contain one kind or two or more kinds of surfactants. Although type of the surfactant is not particularly limited, one kind or two or more kinds of surfactants selected from the group consisting of an ionic surfactant, an ampholytic surfactant, and a nonionic surfactant can be used. Although concentration of the surfactant is not particularly limited, the surfactant can be used at a concentration of about 0.001 to 0.1%, and can be preferably added at a concentration of about 0.005 to 0.05%, based on the total volume of the aqueous composition.

Examples of the ionic surfactant include, for example, cholic acid, deoxycholic acid, and the like, examples of the ampholytic surfactant include, for example, CHAPS (3-[(cholamidopropyl)dimethylammonio]-1-propane-sulfonate), CHAPSO (3-[(3-cholamidopropyl)dimethylammonio]-2-hydroxy-1-propanesulfonate), and the like, and examples of the nonionic surfactant include, for example, those of Tween (registered trademark), TRITON (registered trademark), PLURONIC (registered trademark), Carbowax (registered trademark), and the like. The names mentioned as specific examples of the nonionic surfactant are those representing surfactant series. For example, Tween surfactants include those with product names of Tween 20, Tween 40, Tween 60, Tween 80, and the like. Among them, nonionic surfactants are preferably used in the present invention. Among the nonionic surfactants, Tween 20 and Tween 80 are more preferred, and Tween 80 is especially preferred.

The aqueous composition of the present invention may further contain a buffering agent, and the composition may contain, for example, a buffering agent selected from the group consisting of a phosphate buffering agent, a citrate buffering agent, an acetate buffering agent, a borate buffering agent, a tartrate buffering agent, and a tris buffering agent, and a citrate buffering agent or a phosphate buffering agent can be preferably contained.

When a citrate buffering agent is used, the agent can be used at a concentration of, for example, about 10 to 250 mM, and can be preferably added at a concentration of about 25 to 75 mM. When a phosphate buffering agent or phosphate buffered saline is used, the agent can be used at a concentration of, for example, about 2 to 50 mM, and can be preferably added at a concentration of about 5 to 15 mM. Although pH of the aqueous composition of the present invention is not particularly limited, the composition can be prepared to have a pH value of, for example, 6.5 to 8.0, preferably 7.0 to 7.8, and can be adjusted to have a desired pH value with an appropriate pH modifier such as hydrochloric acid and sodium hydroxide. The aqueous composition of the present invention is preferably prepared so as to be isotonic with body fluids, and can contain an tonicity agent for this purpose. As the tonicity agent, for example, sodium chloride, glycerol, and the like can be used, and sodium chloride can be preferably used.

The aqueous composition of the present invention may contain a polycarboxylic acid selected from the group consisting of EDTA, citric acid, phytic acid, malic acid, and gluconic acid, and can preferably contain EDTA. When a chelating agent is contained, the agent can be used at a concentration of, for example, about 0.1 to 10.0 mg/mL, and can be preferably added at a concentration of about 0.2 to 5.0 mg/mL.

As aqueous medium of the aqueous composition of the present invention, for example, water, distilled water for injection, physiological saline, phosphate buffer, phosphate buffered saline, and the like can be used, and phosphate buffered saline can be preferably used.

Although the method for preparing the aqueous composition of the present invention is not particularly limited, the composition can be prepared by, for example, dissolving follicle-stimulating hormone and histidine in an appropriate aqueous medium such as water, distilled water for injection, physiological saline or phosphate buffered saline, and optionally adding one or two or more kinds of the amino acids, saccharides, propylene glycol, creatinine, surfactants, buffering agents, pH modifiers, tonicity agents, and the like explained above, as required. The composition may be subjected to a sterilization process such as filtration sterilization as required to prepare an aqueous composition for injection. The aqueous composition of the present invention can be used as a pharmaceutical composition for injection for, for example, infertility treatment, and the like.

EXAMPLES

The present invention will be more specifically explained with reference to examples. However, the scope of the present invention is not limited by the following examples.

Example 1

Examination of Remaining Ratio for Amino Acid

Aqueous compositions were prepared by adding a genetic recombinant FSH at 150 IU/mL, sucrose at 50 mg/mL and Tween 80 at 0.01% to a 50 mM citrate buffer, 10 mM phosphate buffered saline (PBS), or 10 mM phosphate buffer (PB), and further adding amino acids (concentration: 0.5 mg/mL) to the mixture in such combinations with the buffers as shown in Table 1 mentioned below. A 0.5 mL-portion of each aqueous composition was put into a 2 mL-volume container, sealed, and stored at 50° C. for two weeks. After the two weeks, the amount of FSH was measured by an immunoassay, and a ratio thereof to the amount of FSH measured at the start of the experiment (remaining ratio) was calculated. The results are shown in Table 1 mentioned below.

TABLE 1

| Test Example No. | Amino acid (0.5 mg/mL) | Buffering agent | Remaining ratio |
|---|---|---|---|
| Example 1-1 | Histidine | Citrate (50 mM, pH 7.4) | 71% |
| Example 1-2 | | PBS (10 mM, pH 7.4) | 76% |
| Example 1-3 | | PB (10 mM, pH 7.4) | 60% |
| Comparative Example 1-1 | Methionine | Citrate (50 mM, pH 7.4) | 69% |
| Comparative Example 1-2 | | PBS (10 mM, pH 7.4) | 70% |
| Comparative Example 1-3 | Sodium aspartate | PBS (10 mM, pH 7.4) | 56% |
| Comparative Example 1-4 | Alanine | " | 55% |

TABLE 1-continued

| Test Example No. | Amino acid (0.5 mg/mL) | Buffering agent | Remaining ratio |
|---|---|---|---|
| Comparative Example 1-5 | Cysteine hydrochloride | " | 2% |
| Comparative Example 1-6 | Glycine | " | 70% |
| Comparative Example 1-7 | Glutamine | " | 60% |
| Comparative Example 1-8 | Glutamic acid hydrochloride | " | 56% |
| Comparative Example 1-9 | Sodium glutamate | " | 54% |
| Comparative Example 1-10 | Oxidized glutathione | " | 59% |
| Comparative Example 1-11 | Cystine | " | 38% |
| Comparative Example 1-12 | Cystine di-hydrochloride | " | 43% |
| Comparative Example 1-13 | Cysteic acid | " | 47% |
| Comparative Example 1-14 | Serine | " | 54% |
| Comparative Example 1-15 | Tyrosine | " | 40% |
| Comparative Example 1-16 | Tryptophan | " | 41% |
| Comparative Example 1-17 | Phenylalanine | " | 44% |
| Comparative Example 1-18 | Proline | " | 52% |
| Comparative Example 1-19 | Leucine | " | 58% |

Example 2

Examination of Remaining Ratio for Combination of Amino Acids

Figure 2:
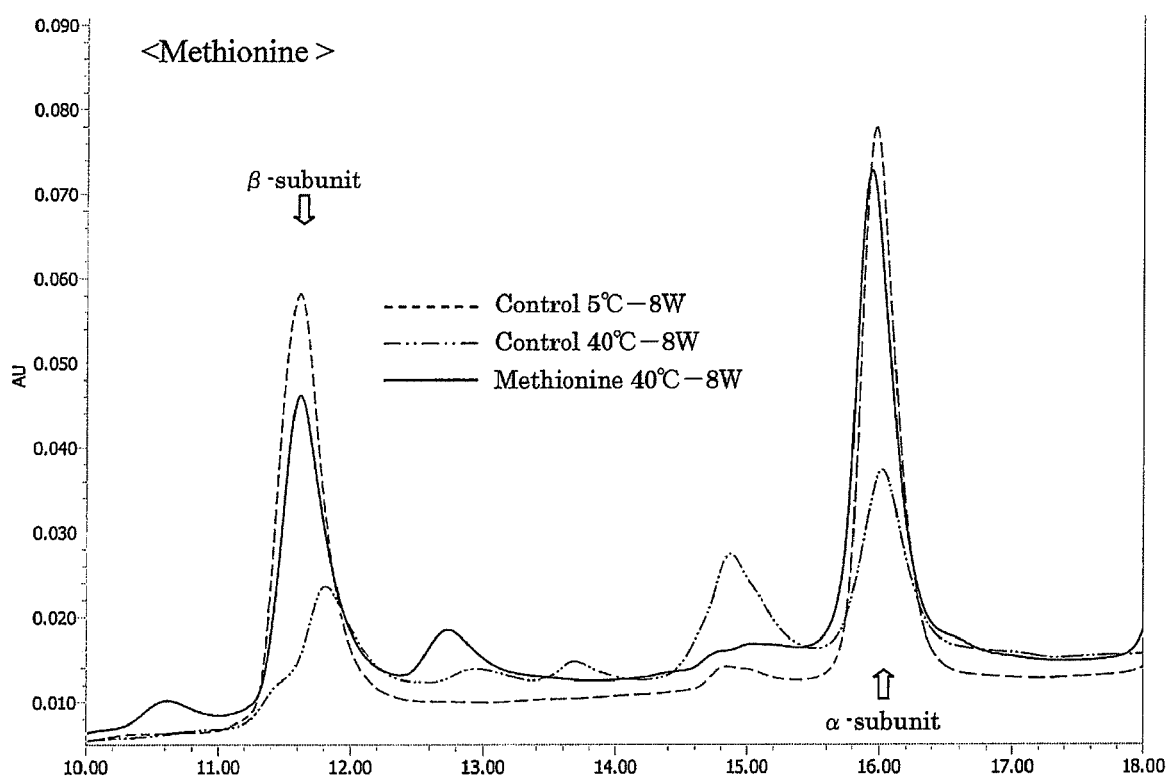
FIG. 2 shows an enlarged view of HPLC charts obtained for follicle-stimulating hormone-containing compositions around the peaks of the α-subunit and β-subunit. The charts were obtained for a composition prepared by adding a genetic recombinant FSH at 150 IU/mL, sucrose at 50 mg/mL and Tween 80 at 0.01% to 10 mM PBS, and further adding methionine to the mixture, after storage thereof at 40° C. for 8 weeks, and a composition prepared by adding a genetic recombinant FSH at 150 IU/mL and Tween 80 at 0.01% to 10 mM PBS, after storage thereof at 5° C. or 40° C. for 8 weeks.
Figure 3:
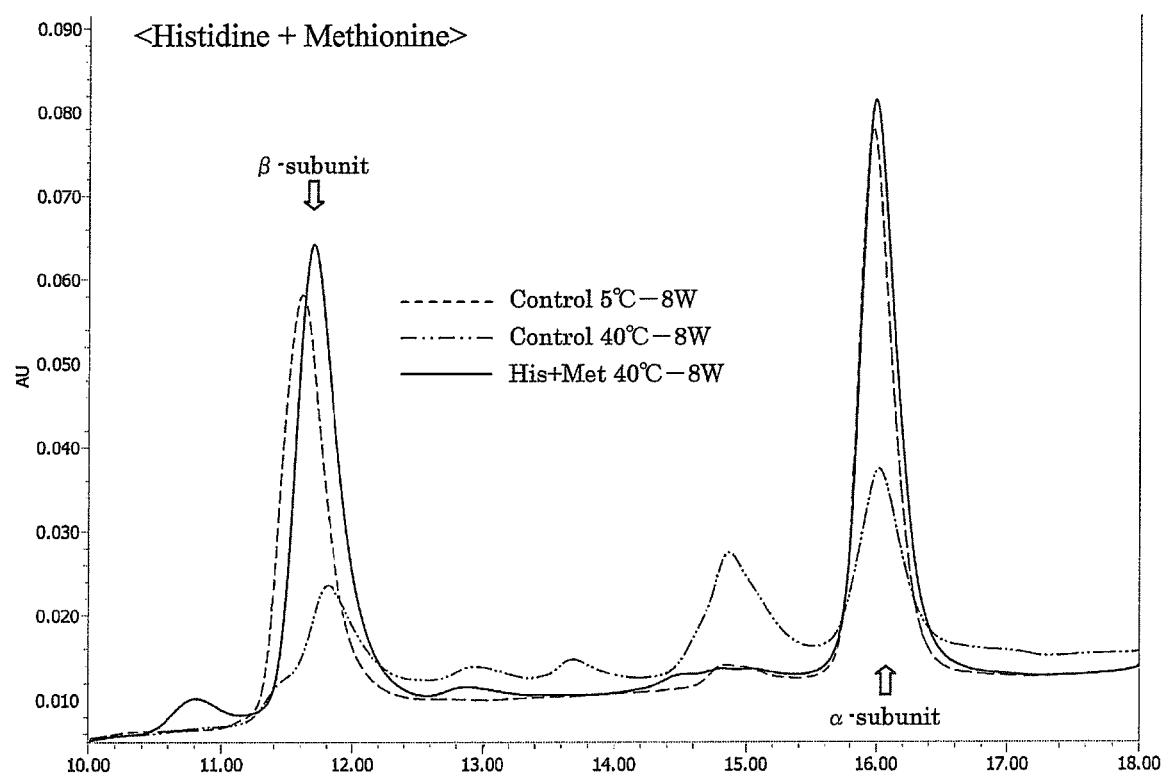
FIG. 3 shows an enlarged view of HPLC charts obtained for follicle-stimulating hormone-containing compositions around the peaks of the α-subunit and β-subunit. The charts were obtained for a composition prepared by adding a genetic recombinant FSH at 150 IU/mL, sucrose at 50 mg/mL and Tween 80 at 0.01% to 10 mM PBS, and further adding methionine and histidine to the mixture, after storage thereof at 40° C. for 8 weeks, and a composition prepared by adding a genetic recombinant FSH at 150 IU/mL and Tween 80 at 0.01% to 10 mM PBS, after storage thereof at 5° C. or 40° C. for 8 weeks.

Aqueous compositions were prepared by adding a genetic recombinant FSH at 150 IU/mL, sucrose at 50 mg/mL and Tween 80 at 0.01% to 10 mM PBS, and further adding histidine and/or methionine to the mixture as shown in Table 2 mentioned below at the respective concentrations. As a control, an aqueous composition was prepared by adding a genetic recombinant FSH at 150 IU/mL and Tween 80 at 0.01% to 10 mM PBS. A 0.5 mL-portion of each aqueous composition was put into a 2 mL-volume container, sealed, and stored at 40° C. for 8 weeks. At the start of the experiment, and after 5 weeks and 8 weeks, each aqueous composition was analyzed by reverse phase HPLC (HPLC charts obtained after 8 weeks are shown in FIGS. 1 to 3), and the obtained values of peak areas of α-subunit and β-subunit were corrected on the basis of the values of peak areas of the subunits obtained with a FSH standard sample (10 µg/mL frozen genetic recombinant FSH solution stored at −80° C., thawed before use). Then, remaining ratios of the subunits in the aqueous compositions were calculated after the periods as ratios of the amounts measured after the periods to the amounts measured at the start of the experiment. The amounts of FSH were calculated by totaling the peak area values of the subunits. The results are shown in Table 2 mentioned below.

TABLE 2

| Test Example No. | Amino acid | | Remaining ratio (%) | |
|---|---|---|---|---|
| | | | 5 weeks | 8 weeks |
| Example 2-1 | Histidine (0.5 mg/mL) | α-subunit | 86.3 | 79.8 |
| | | β-subunit | 87.8 | 86.6 |
| | | FSH | 87.1 | 83.4 |

TABLE 2-continued

| Test Example No. | Amino acid | | Remaining ratio (%) | |
|---|---|---|---|---|
| | | | 5 weeks | 8 weeks |
| Comparative Example 2 | Methionine (0.5 mg/mL) | α-subunit | 112.1 | 104.9 |
| | | β-subunit | 87.0 | 70.6 |
| | | FSH | 99.2 | 87.2 |
| Example 2-2 | Histidine (0.5 mg/mL) + Methionine (0.5 mg/mL) | α-subunit | 112.2 | 110.0 |
| | | β-subunit | 98.2 | 93.8 |
| | | FSH | 104.8 | 101.5 |
| Control | — | α-subunit | 60.3 | 56.0 |
| | | β-subunit | 44.0 | 39.0 |
| | | FSH | 51.7 | 47.1 |

From these measurement results, it can be understood that histidine and methionine show high stabilization effect for the α-subunit and β-subunit, respectively. Further, the FSH preparation containing both histidine and methionine as stabilizing agents was extremely stable.

Example 3

Examination of Remaining Ratio for Concentration of Histidine

Aqueous compositions were prepared by adding a genetic recombinant FSH at 150 IU/mL, sucrose at 50 mg/mL and Tween 80 at 0.01% to a 50 mM citrate buffer or 10 mM PBS, and further adding histidine to the mixture in the combinations shown in Table 3 mentioned below, and the remaining ratio was examined in the same manner as that of Example 1. The results are shown in Table 3 mentioned below.

TABLE 3

| Test Example No. | Histidine concentration | Buffer | Remaining ratio |
|---|---|---|---|
| Example 3-1 (Comparative Example) | 0 mg/mL | PBS (10 mM, pH 7.4) | 60% |
| Example 3-2 | 0.2 mg/mL | Citrate (50 mM, pH 7.4) | 71% |
| Example 3-3 | | PBS (10 mM, pH 7.4) | 68% |
| Example 1-1 | 0.5 mg/mL | Citrate (50 mM, pH 7.4) | 71% |
| Example 1-2 | | PBS (10 mM, pH 7.4) | 76% |
| Example 1-3 | | PB (10 mM, pH 7.4) | 60% |
| Example 3-4 | 1.0 mg/mL | Citrate (50 mM, pH 7.4) | 74% |
| Example 3-5 | | PBS (10 mM, pH 7.4) | 73% |
| Example 3-6 | 2.0 mg/mL | Citrate (50 mM, pH 7.4) | 71% |
| Example 3-7 | | PBS (10 mM, pH 7.4) | 75% |
| Example 3-8 | 3.2 mg/mL | Citrate (50 mM, pH 7.4) | 74% |
| Example 3-9 | | PBS (10 mM, pH 7.4) | 70% |

Example 4

Examination and Comparison of Remaining Ratio for Saccharide

Aqueous compositions were prepared by adding a genetic recombinant FSH at 150 IU/mL, histidine at 0.5 mg/mL and Tween 80 at 0.01% to a 50 mM citrate buffer or 10 mM PBS, and further adding a saccharide, propylene glycol or creatinine to the mixture in the combinations shown in Table 4 mentioned below, and the remaining ratio was examined in the same manner as that of Example 1. The results are shown in Table 4 mentioned below. The results obtained by not adding histidine are also shown as comparative examples.

TABLE 4

| Test Example No. | Saccharide (concentration) | Buffer | Remaining ratio |
|---|---|---|---|
| Example 1-1 | Sucrose (50 mg/mL) | Citrate (50 mM, pH 7.4) | 71% |
| Example 1-2 | " | PBS (10 mM, pH 7.4) | 76% |
| Example 4-1 | Sucrose (10 mg/mL) | " | 70% |
| Example 4-2 | Inositol (50 mg/mL) | Citrate (50 mM, pH 7.4) | 79% |
| Example 4-3 | " | PBS (10 mM, pH 7.4) | 78% |
| Example 4-4 | Inositol (10 mg/mL) | " | 70% |
| Example 4-5 | Xylitol (50 mg/mL) | Citrate (50 mM, pH 7.4) | 79% |
| Example 4-6 | " | PBS (10 mM, pH 7.4) | 81% |
| Example 4-7 | Xylitol (10 mg/mL) | " | 64% |
| Example 4-8 | Glycerol (50 mg/mL) | " | 37% |
| Example 4-9 | Glucose (50 mg/mL) | " | 56% |
| Example 4-10 | Calcium gluconate (1 mg/mL) | Citrate (50 mM, pH 7.4) | 70% |
| Example 4-11 | " | PBS (10 mM, pH 7.4) | 73% |
| Example 4-12 | Calcium gluconate (0.2 mg/mL) | " | 68% |
| Example 4-13 | Creatinine (25 mg/mL) | " | 69% |
| Example 4-14 | Creatinine (5 mg/mL) | " | 71% |
| Example 4-15 | Sorbitol (50 mg/mL) | " | 67% |
| Example 4-16 | Dextran 70 (50 mg/mL) | " | 59% |
| Example 4-17 | Fructose (50 mg/mL) | " | 21% |
| Example 4-18 | Propylene glycol (50 mg/mL) | " | 78% |
| Example 4-19 | Macrogol 400 (50 mg/mL) | " | 67% |
| Example 4-20 | Macrogol 600 (50 mg/mL) | Citrate (50 mM, pH 7.4) | 67% |
| Example 4-21 | " | PBS (10 mM, pH 7.4) | 72% |
| Example 4-22 | Macrogol 600 (10 mg/mL) | " | 67% |
| Example 4-23 | Macrogol 4000 (50 mg/mL) | " | 61% |
| Example 4-24 | Maltose (50 mg/mL) | " | 58% |
| Example 4-25 | Mannitol (50 mg/mL) | Citrate (50 mM, pH 7.4) | 80% |
| Example 4-26 | " | PBS (10 mM, pH 7.4) | 73% |
| Example 4-27 | Mannitol (10 mg/mL) | " | 70% |
| Example 4-28 | Lactose (50 mg/mL) | " | 54% |
| Comparative Example 4-1 | Sucrose (50 mg/mL) | " | 60% |
| Comparative Example 4-2 | Inositol (50 mg/mL) | " | 56% |
| Comparative Example 4-3 | Xylitol (50 mg/mL) | " | 63% |

TABLE 4-continued

| Test Example No. | Saccharide (concentration) | Buffer | Remaining ratio |
|---|---|---|---|
| Comparative Example 4-4 | Calcium gluconate (1 mg/mL) | " | 76% |
| Comparative Example 4-5 | Calcium gluconate (0.2 mg/mL) | " | 55% |
| Comparative Example 4-6 | Creatinine (25 mg/mL) | " | 54% |
| Comparative Example 4-7 | Creatinine (5 mg/mL) | " | 61% |
| Comparative Example 4-8 | Macrogol 600 (50 mg/mL) | " | 32% |
| Comparative Example 4-9 | Macrogol 600 (10 mg/mL) | " | 71% |
| Comparative Example 4-10 | Mannitol (50 mg/mL) | " | 64% |

Example 5

Examination and Comparison of Remaining Ratio for Surfactant

Aqueous compositions were prepared by adding a genetic recombinant FSH at 150 IU/mL, histidine at 0.5 mg/mL and sucrose at 50 mg/mL to a 50 mM citrate buffer, 10 mM PBS or 10 mM PB, and further adding a surfactant to the mixture in such combinations with the buffers as shown in Table 5 mentioned below, and the remaining ratios of FSH in the compositions were examined in the same manner as that of Example 1. The results are shown in Table 5 mentioned below. The results obtained by adding 0.5 mg/mL of methionine instead of 0.5 mg/mL of histidine are also shown as comparative examples. The stability was indicated as the ratio of the FSH amount measured 2 weeks after the start of the experiment to the FSH amount measured at the start of the experiment. When no surfactant was added, adsorption or the like took place when the compositions were put into vials, and the FSH amount was reduced to about 80% of that observed with adding a surfactant at that time.

TABLE 5

| Example No. | Surfactant | Buffering agent | Remaining ratio |
|---|---|---|---|
| Example 1-1 | Tween 80 (0.01%) | Citrate (50 mM, pH 7.4) | 71% |
| Example 1-2 | | PBS (10 mM, pH 7.4) | 76% |
| Example 1-3 | | PB (10 mM, pH 7.4) | 60% |
| Comparative Example 1-1 | | Citrate (50 mM, pH 7.4) | 69% |
| Comparative Example 1-2 | | PBS (10 mM, pH 7.4) | 70% |
| Example 5-1 | Tween 20 (0.01%) | Citrate (50 mM, pH 7.4) | 77% |
| Example 5-2 | | PBS (10 mM, pH 7.4) | 73% |
| Example 5-3 | | PB (10 mM, pH 7.4) | 58% |
| Comparative Example 5-1 | | Citrate (50 mM, pH 7.4) | 72% |
| Example 5-4 | None | PBS (10 mM, pH 7.4) | 65% |
| Example 5-5 | | PB (10 mM, pH 7.4) | 46% |

INDUSTRIAL APPLICABILITY

The aqueous composition of the present invention is useful as a stable pharmaceutical composition in which reduction of the activity during storage and distribution is eliminated.

What is claimed is:

1. An aqueous composition comprising purified or isolated follicle-stimulating hormone, a buffer selected from the group consisting of a phosphate buffer and a citrate buffer, and histidine as a free amino acid.

2. The aqueous composition according to claim 1, wherein the concentration of histidine is 0.05 to 10.0 mg/mL.

3. The aqueous composition according to claim 1, which comprises a genetic recombinant human follicle-stimulating hormone as the follicle-stimulating hormone.

4. The aqueous composition according to claim 1, which further comprises one or more substances selected from the group consisting of a saccharide, propylene glycol, and creatinine.

5. The aqueous composition according to claim 1, which further comprises one or more substances selected from the group consisting of xylitol, inositol, propylene glycol, sucrose, calcium gluconate, sodium gluconate, mannitol, macrogol 600, and creatinine.

6. The aqueous composition according to claim 1, which further comprises methionine.

7. The aqueous composition according to claim 6, wherein the concentration of methionine is 0.05 to 10 mg/mL.

8. The aqueous composition according to claim 1, which further comprises a surfactant.

9. The aqueous composition according to claim 8, wherein the surfactant is a nonionic surfactant.

10. The aqueous composition according to claim 1, which has a pH value of 6.5 to 8.0.

11. The aqueous composition according to claim 1, which further comprises sodium chloride.

12. The aqueous composition according to claim 1, which further comprises EDTA.

13. The aqueous composition according to claim 1, comprising a phosphate buffer, which is phosphate buffered saline.

* * * * *